US009429479B2

(12) United States Patent
Millar et al.

(10) Patent No.: US 9,429,479 B2
(45) Date of Patent: Aug. 30, 2016

(54) METHODS, DEVICES, AND SYSTEMS WHICH DETERMINE A PARAMETER VALUE OF AN OBJECT OR AN ENVIRONMENT FROM A VOLTAGE READING ASSOCIATED WITH A COMMON MODE SIGNAL OF A BALANCED CIRCUIT

(75) Inventors: Huntly D. Millar, Houston, TX (US); Richard T. Thornton, Bacliff, TX (US); Robert L. Pauly, Friendswood, TX (US)

(73) Assignee: Millar Instruments, Houston, TX (US)

( * ) Notice: Subject to any disclaimer, the term of this patent is extended or adjusted under 35 U.S.C. 154(b) by 679 days.

(21) Appl. No.: 13/551,811

(22) Filed: Jul. 18, 2012

(65) Prior Publication Data

US 2014/0023112 A1    Jan. 23, 2014

(51) Int. Cl.
*G01K 3/08* (2006.01)
*G01K 7/20* (2006.01)
*G01K 13/00* (2006.01)
*G01L 1/22* (2006.01)
*G01L 9/04* (2006.01)
*G01L 9/06* (2006.01)

(52) U.S. Cl.
CPC ............... *G01K 7/20* (2013.01); *G01K 13/002* (2013.01); *G01L 1/2262* (2013.01); *G01L 1/2281* (2013.01); *G01L 9/045* (2013.01); *G01L 9/065* (2013.01)

(58) Field of Classification Search
CPC .................................. G01K 7/20; G01K 7/16
USPC ....... 374/100, 163, 185, 114, 141, 143, 183, 374/179, 45; 600/474, 549; 702/130, 131, 702/133
See application file for complete search history.

(56) References Cited

U.S. PATENT DOCUMENTS

| | | | | | |
|---|---|---|---|---|---|
| 3,494,196 A | * | 2/1970 | Moussette | ..................... | 374/183 |
| 3,702,076 A | * | 11/1972 | Georgi | .......................... | 374/169 |
| 3,776,040 A | * | 12/1973 | Gould, III | ..................... | 374/185 |
| 4,023,094 A | * | 5/1977 | Adams | ......................... | 324/610 |
| 4,143,549 A | * | 3/1979 | Koehler | ................... | G01K 7/24 374/114 |
| 4,150,786 A | * | 4/1979 | Sable | ...................... | G01K 3/08 165/287 |

(Continued)

FOREIGN PATENT DOCUMENTS

GB          2251948          7/1992

OTHER PUBLICATIONS

International Search Report & Written Opinion dated Apr. 10, 2014 for PCT/US2013/050311.

*Primary Examiner* — Gail Kaplan Verbitsky
(74) *Attorney, Agent, or Firm* — Egan, Peterman, Enders & Huston LLP

(57) ABSTRACT

A method for determining a value of a parameter of an object or an environment includes positioning a device having a balanced circuit in or on an object or within a particular environment, wherein the balanced circuit comprises elements which are operationally sensitive to changes in a parameter of the object or the environment. The method further includes measuring a common mode signal of the balanced circuit and determining, from the common mode signal, a value of the parameter. An exemplary implementation of the method includes determining temperature using a resistive sensor having a Wheatstone bridge circuit with two variable resistors and two fixed resistors. Embodiments of systems and devices configured to employ such methods are provided, particularly medical probes, electronic signal monitoring devices, and systems employing such devices.

6 Claims, 4 Drawing Sheets

(56) References Cited

U.S. PATENT DOCUMENTS

| | | | | |
|---|---|---|---|---|
| 4,183,248 A * | 1/1980 | West | | 374/164 |
| 4,201,088 A * | 5/1980 | Trietley, Jr. | | G01D 1/10 |
| | | | | 374/114 |
| 4,411,257 A * | 10/1983 | Machida | | 600/117 |
| 4,465,075 A * | 8/1984 | Swartz | | G01L 9/045 |
| | | | | 600/485 |
| 4,528,637 A * | 7/1985 | Smith | | 702/133 |
| 4,554,927 A * | 11/1985 | Fussell | | 600/483 |
| 4,659,235 A * | 4/1987 | Gilmore et al. | | 374/143 |
| 4,729,242 A * | 3/1988 | Reich | | G01L 21/12 |
| | | | | 374/143 |
| 4,817,022 A * | 3/1989 | Jornod | | G01L 13/025 |
| | | | | 702/98 |
| 5,475,623 A * | 12/1995 | Stocker | | G01L 21/12 |
| | | | | 327/350 |
| 5,686,826 A | 11/1997 | Kurtz et al. | | |
| 5,902,248 A | 5/1999 | Millar et al. | | |
| 6,329,825 B1 * | 12/2001 | Tanaka et al. | | 324/725 |
| 6,394,986 B1 | 5/2002 | Millar | | |
| 6,433,554 B1 * | 8/2002 | Kawate | | G01D 3/022 |
| | | | | 324/500 |
| 6,441,674 B1 * | 8/2002 | Lin | | 327/512 |
| 6,938,493 B2 * | 9/2005 | Bills | | G01L 21/12 |
| | | | | 257/467 |
| 7,191,072 B2 | 3/2007 | Champion et al. | | |
| 7,392,703 B2 * | 7/2008 | Zhao | | G01P 15/18 |
| | | | | 73/514.05 |
| 7,803,121 B2 | 9/2010 | Plouf et al. | | |
| 8,092,084 B2 * | 1/2012 | Riddle et al. | | 374/185 |
| 8,197,133 B2 * | 6/2012 | Schultz et al. | | 374/170 |
| 8,348,501 B2 * | 1/2013 | Severson | | 374/16 |
| 8,482,872 B1 * | 7/2013 | Contreras | | G11B 5/6005 |
| | | | | 360/31 |
| 8,562,210 B2 * | 10/2013 | Abadeer et al. | | 374/185 |
| 8,708,555 B2 * | 4/2014 | Shipley et al. | | 374/5 |
| 2002/0049559 A1 * | 4/2002 | Hamilton et al. | | 702/127 |
| 2004/0155644 A1 * | 8/2004 | Stauth | | G01R 33/09 |
| | | | | 324/117 R |
| 2004/0245585 A1 * | 12/2004 | Johnson | | 257/414 |
| 2005/0274187 A1 * | 12/2005 | Zhao | | G01P 15/18 |
| | | | | 73/514.16 |
| 2006/0052968 A1 * | 3/2006 | Miller | | G01D 3/036 |
| | | | | 702/127 |
| 2007/0016384 A1 * | 1/2007 | Edward Niblock | | F02B 77/085 |
| | | | | 702/130 |
| 2007/0019704 A1 * | 1/2007 | Sultan | | G01K 7/42 |
| | | | | 374/141 |
| 2007/0113667 A1 * | 5/2007 | Stratton | | G01K 5/52 |
| | | | | 73/755 |
| 2007/0295094 A1 * | 12/2007 | Kurtz et al. | | 73/714 |
| 2009/0013791 A1 | 1/2009 | Zdeblick et al. | | |
| 2011/0098584 A1 | 4/2011 | Plouf et al. | | |
| 2013/0176643 A1 * | 7/2013 | Contreras | | G11B 5/6005 |
| | | | | 360/235.4 |
| 2014/0067288 A1 * | 3/2014 | Kurtz | | G01L 15/00 |
| | | | | 702/53 |
| 2015/0192478 A1 * | 7/2015 | Rueth | | G01L 9/00 |
| | | | | 374/143 |
| 2015/0297094 A1 * | 10/2015 | Malpas | | A61M 27/006 |
| | | | | 600/549 |

* cited by examiner

METHODS, DEVICES, AND SYSTEMS WHICH DETERMINE A PARAMETER VALUE OF AN OBJECT OR AN ENVIRONMENT FROM A VOLTAGE READING ASSOCIATED WITH A COMMON MODE SIGNAL OF A BALANCED CIRCUIT

BACKGROUND OF THE INVENTION

1. Field of the Invention

This invention generally relates to methods, devices and systems for determining parameter values of objects and environments and, more specifically, to methods, devices and systems which utilize a voltage reading associated with a common mode signal of a balanced circuit to determine a value of a parameter of an object or an environment.

2. Description of the Related Art

The following descriptions and examples are not admitted to be prior art by virtue of their inclusion within this section.

Many sensors employ balanced circuits for determining information. In particular, a balanced circuit may be configured such that information of interest for a sensor may be determined from a differential voltage between the output nodes of the balanced circuit. More specifically, each line of a balanced circuit may be configured with elements which are operationally sensitive to changes in a parameter of an object or an environment in which the balanced circuit is disposed and each of the elements may be configured to alter the voltage along its respective line in an opposing manner. In general, it is the objective of such balanced circuits to have signal lines of matched impedances such that noise and interference induced in each of the lines does not substantially affect the accuracy of the differential voltage measurement attributed to the information of interest. In particular, having matched impedances on each signal line allows noise and interference signals to be canceled for a differential voltage measurement. On the contrary, any inequality in the noise and/or interference induced in each line will result in such signals not being fully cancelled.

In order to ensure the accuracy of a differential voltage measurement, a common mode voltage between the signal output nodes of the balanced circuit is often monitored. In particular, a common mode voltage of a presumably balanced circuit is monitored relative to a target voltage or relative to the differential gain of the circuit, the latter scenario of which is referred to as a common-mode rejection ratio. The term "common mode voltage" refers to the voltage at a given location that appears equally and in phase from each signal conductor to a common reference. Alternatively stated, the term "common mode voltage" refers to the instantaneous algebraic average of two signals within a balanced circuit with both signals referenced to a common reference. Although both differential mode and common mode signals are analyzed when using a balanced circuit, they are generally referenced as "wanted signals" and "unwanted signals," respectively. In particular, differential mode signal measurements relate directly to determining the value of a parameter being measured by a sensor and, thus, are considered "wanted." In contrast, common mode signal measurements reflect the portions of the signals which do not contribute to determining the information of interest for a sensor and, thus, are considered "unwanted." In other words, common mode signal measurements are only monitored in conventional practices for determining whether to accept or throw out differential mode signal measurements relating to a variable parameter.

SUMMARY OF THE INVENTION

The following description of various embodiments of methods, devices and systems is not to be construed in any way as limiting the subject matter of the appended claims.

Embodiments of a method for determining a value of a parameter of an object or an environment includes positioning a device having a balanced circuit in or on an object or within a particular environment, wherein the balanced circuit comprises elements which are operationally sensitive to changes in a parameter of the object or the environment. In addition, the method includes measuring a voltage derived from the balanced circuit which correlates to a common mode signal of the balanced circuit and determining, from the measured voltage, a value of the parameter.

Embodiments of a method for determining temperature using a resistive sensor having a Wheatstone bridge circuit with at least two variable resistors includes positioning the resistive sensor such that the at least two variable resistors of the Wheatstone bridge circuit are arranged in an environment in which temperature is to be determined. The method further includes measuring, while the two variable resistors are arranged in the environment, a temperature detection voltage between a first voltage derived from the Wheatstone bridge circuit which is proportional to a summed voltage of signal output nodes of the Wheatstone bridge circuit and a second voltage which is proportional to a reference voltage for the Wheatstone bridge circuit. Moreover, the method includes determining, from the temperature detection voltage, a temperature of the environment.

Embodiments of medical probes include a Wheatstone bridge circuit with at least two variable resistors and temperature detection circuitry coupled to the Wheatstone bridge circuit which generates a voltage which is proportional to a summed voltage of signal output nodes of the Wheatstone bridge circuit. The medical probes further include compensation circuitry coupled to the Wheatstone bridge circuit which is configured to compensate for variations of a resistive coefficient of a conductive material comprising the Wheatstone bridge circuit due to ambient temperature changes of the conductive material.

Embodiments of electronic signal monitoring devices for monitoring and processing signals received from a balanced circuit of a medical probe include a first means for receiving output signals from the balanced circuit. In addition, the electronic signal monitoring devices include a second means for determining from one or more of the received output signals a voltage which correlates to a common mode signal of the balanced circuit. Moreover, the electronic signal monitoring device includes program instructions which are executable by a processor for determining, from the voltage, a temperature of an environment in which a tip of the medical probe is arranged.

Embodiments of systems include a medical probe having a resistive sensor with a Wheatstone bridge circuit having at least two variable resistors. The systems further include an electronic signal monitoring device configured for electrical electrical communication with the medical probe to measure electrical parameters of the resistive sensor. Moreover, the systems include temperature detection circuitry coupled to the Wheatstone bridge circuit that is configured to generate a first voltage which is proportional to a summed voltage of signal output nodes of the Wheatstone bridge circuit. The electronic signal monitoring device includes a means for measuring a temperature detection voltage between the first voltage and a second voltage which is proportional to a reference voltage for the Wheatstone bridge circuit. The systems further include a storage medium with program instructions which are executable by a processor for determining, from the temperature detection voltage, a temperature of an environment in which a tip of the medical probe is arranged.

BRIEF DESCRIPTION OF THE DRAWINGS

Other objects and advantages of the invention will become apparent upon reading the following detailed description and upon reference to the accompanying drawings in which.

Figure 1:
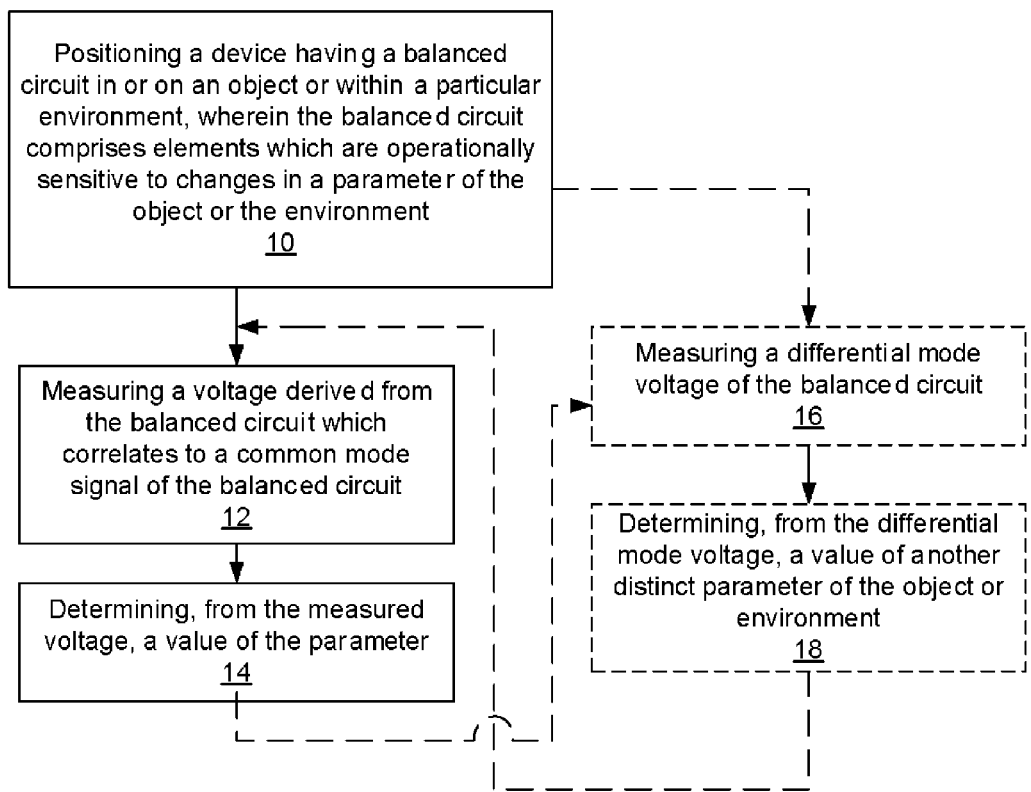
FIG. 1 is a flowchart of a method for determining a value of a parameter of an object or an environment.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 2:
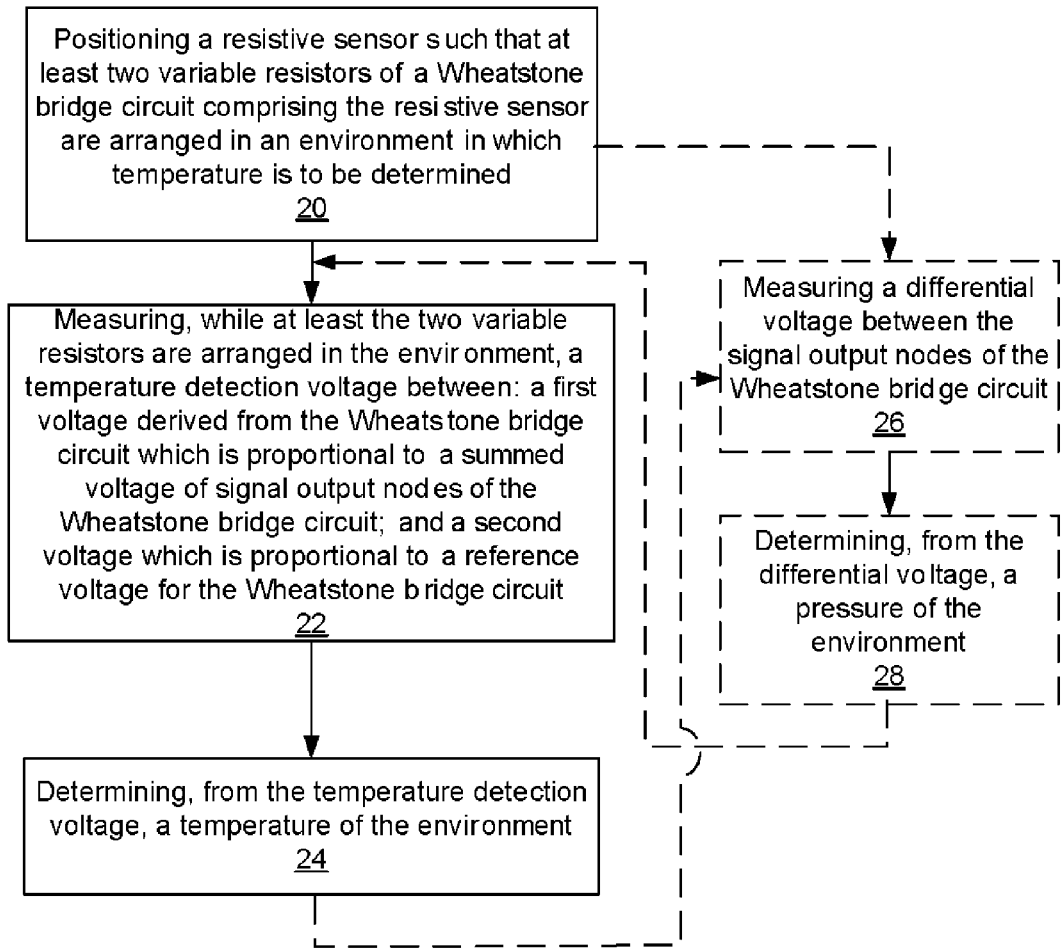
FIG. 2 is a flowchart of a method for determining temperature of an environment using a resistive sensor.
Figure 3:
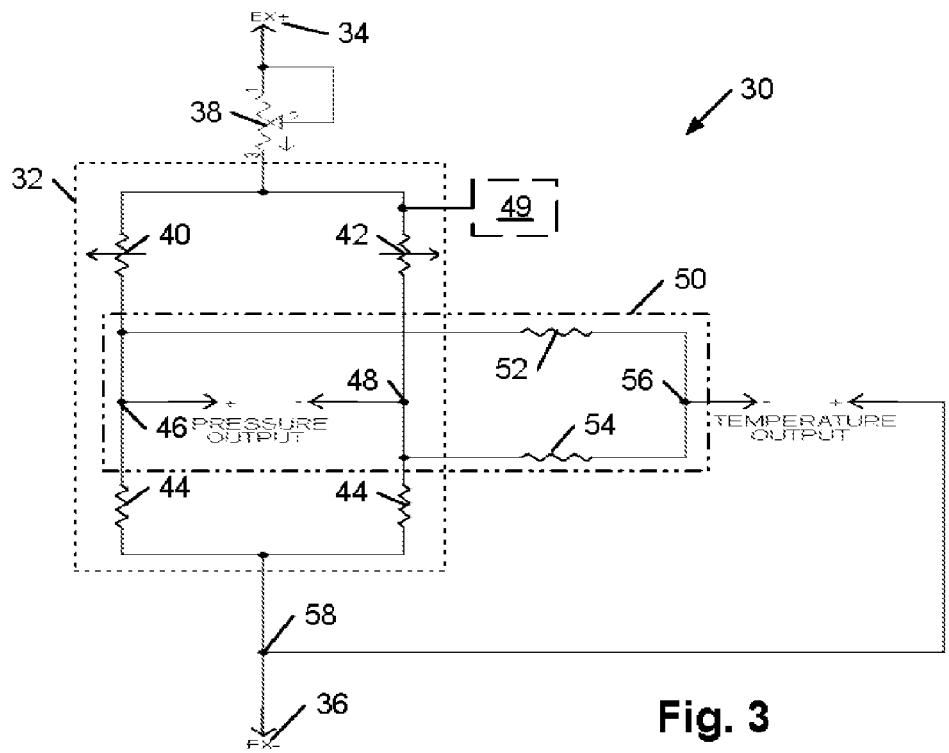
FIG. 3 is a schematic diagram of an exemplary circuit which may be utilized in the method outlined in FIG. 2.
Figure 4:
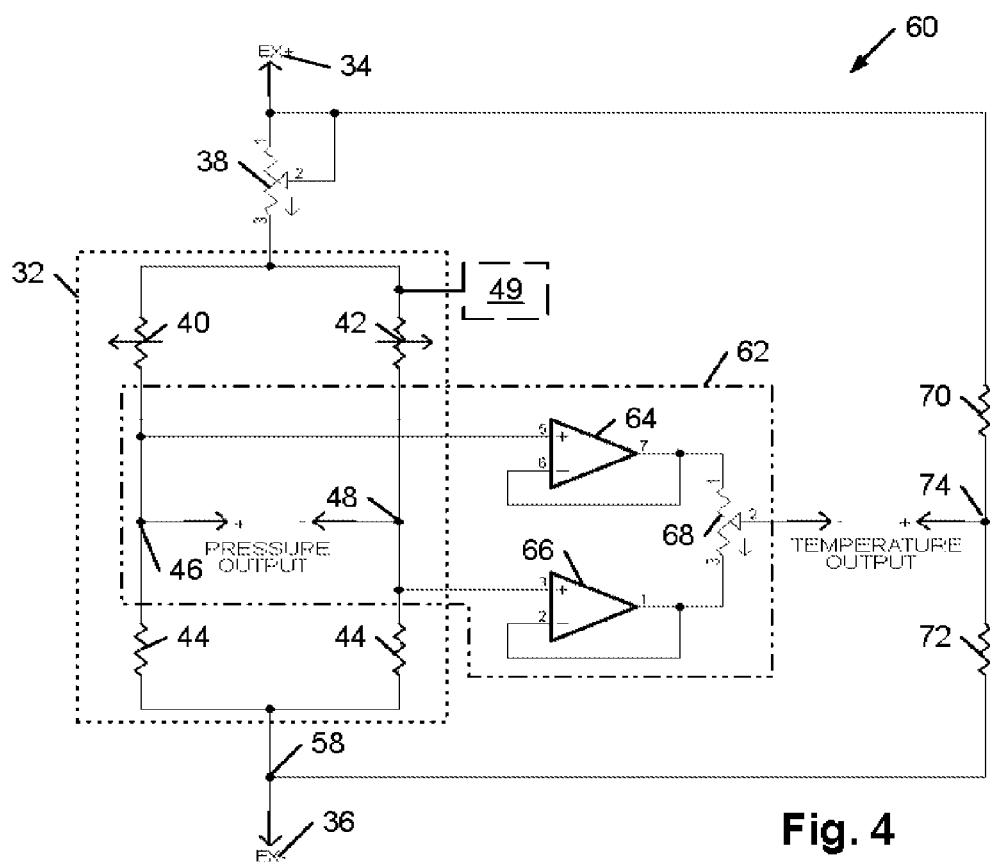
FIG. 4 is a schematic diagram of another exemplary circuit which may be utilized in the method outlined in FIG. 2.
Figure 5:
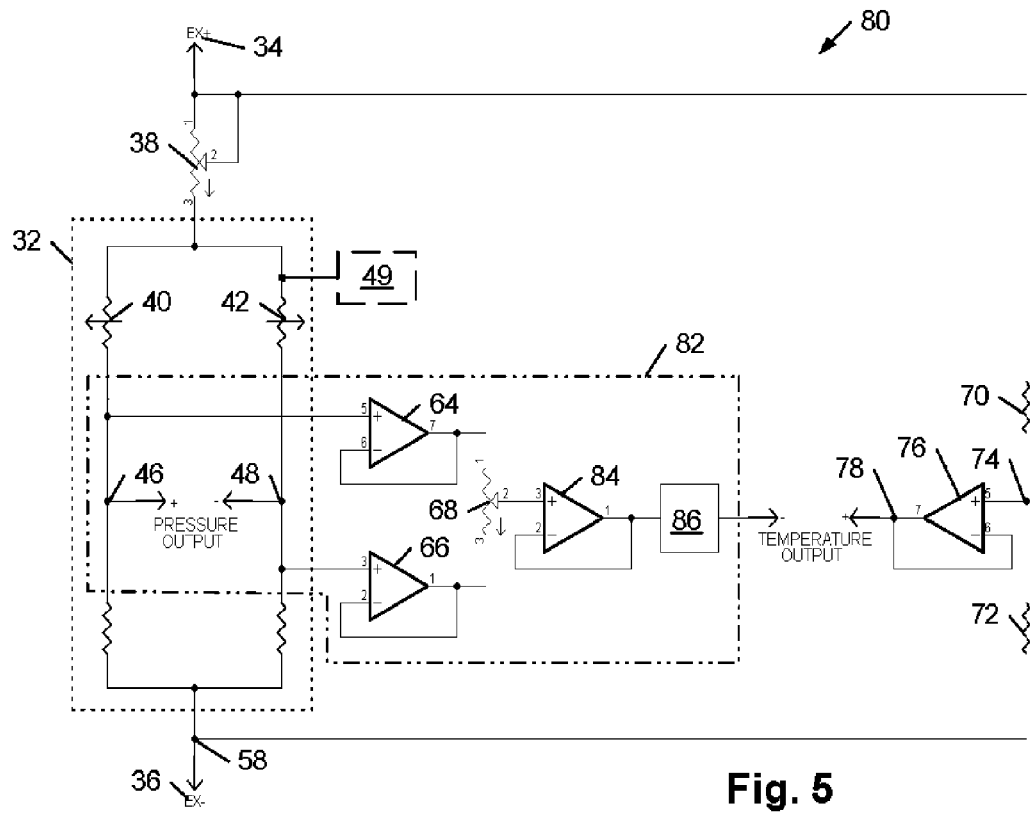
FIG. 5 is a schematic diagram of yet another exemplary circuit which may be utilized in the method outlined in FIG. 2.
Figure 6:
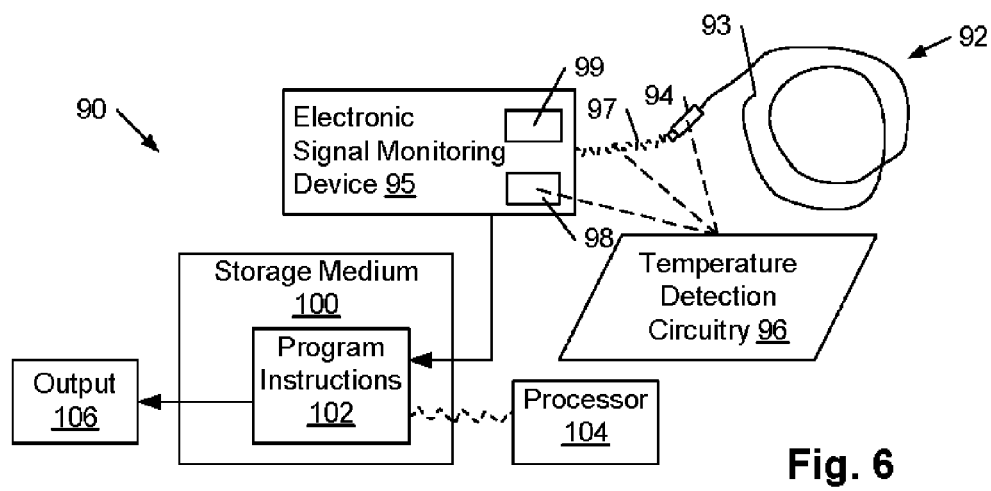
FIG. 6 is a schematic diagram of a medical probe system for determining temperature of an environment in which a medical probe is arranged.

Turning to the drawings, a flowchart of a method for determining a value of a parameter of an object or an environment is shown in FIG. 1. A specific application of such a method utilizing a resistive sensor for determining temperature of an environment is outlined in a flowchart depicted in FIG. 2. FIGS. 3-5 depict schematic diagrams of exemplary circuits which may be utilized in the method outlined in FIG. 2. FIG. 6 illustrates an exemplary system configured to perform the method outlined in FIG. 2. In particular, FIG. 6 illustrates a schematic diagram of a medical probe system for determining temperature of an environment in which a medical probe is arranged. Although FIGS. 3-5 are specifically directed to methods and circuits involving a resistive sensor with a Wheatstone bridge circuit having two variable resistors and two fixed resistors and FIG. 6 is specific to systems and devices involving medical probes, the methods, systems and devices encompassed by the disclosure provided herein are not so restricted. Furthermore, although FIGS. 2-6 are described for determining temperature of an object or environment, the methods, systems and devices provided herein are not so limited.

Rather, as encompassed by the flowchart of FIG. 1, the methods, systems and devices considered herein may involve any device having a balanced circuit which includes elements which are operationally sensitive to changes in a parameter of an object or an environment. The device may be any tool, mechanism or physical means which can accommodate the balanced circuit and which can be placed in proximity to, on, or within an object or environment of interest. The balanced circuit may be of any configuration having any type of operationally sensitive elements known in the art. Thus, the methods, systems and devices described herein are not limited to use of resistive sensors. Furthermore, the methods, systems and devices considered herein may be used to determine any measurable parameter of interest which relates to operationally sensitive elements of a balanced circuit and, moreover, may be used on or within any object or environment in which a device having the balanced circuit can access. As such, the methods, systems and devices considered herein are not restricted to determining a temperature of an object or an environment, much less an environment in which a medical probe is arranged. It is noted that applications and devices alternative to those disclosed in reference to FIGS. 2-6 are provided throughout this disclosure, but the citation of such should not be construed to limit the scope of the methods, systems and devices which may encompass the method outlined in FIG. 1.

Turning to FIG. 1, the flowchart includes block 10 for positioning a device having a balanced circuit in or on an object or within a particular environment, wherein the balanced circuit comprises elements which are operationally sensitive to changes in a parameter of the object or the environment. As set forth in detail below in reference to FIGS. 2-6, an example of an applicable balanced circuit for the device is a silicon strain gauge, such as a Wheatstone bridge circuit, having at least one gauge configured to increase in resistance with a change in pressure and at least one other gauge configured to decrease in resistance with the change in pressure. The balanced circuits encompassed by the methods, systems and devices disclosed herein, however, are not restricted to being operationally sensitive to pressure nor are they restricted to being silicon strain gauges. In particular, other types of parameter sensitive elements and/or balanced circuits may be used, including but not limited to those which may be sensitive to changes in acceleration, tension, force, temperature, volume, velocity, pH, oxygen concentration or humidity.

Similar to the balanced circuit, the device employing the balanced circuit and the object and/or environment in which the device is placed may vary. As noted above, the device may be any tool, mechanism or physical means which can accommodate the balanced circuit and which can be placed in proximity, on, or within an object or environment of interest. Furthermore, the object or environment of interest may be any object or environment having a variable parameter that is desired to be measured. As an example, FIGS. 2-6 describe methods, device and systems in which temperature is the variable parameter desired for measurement and FIG. 6 discusses an exemplary implementation of a medical probe system for measuring temperature of a bodily fluid, a body part or a body cavity. As noted above, however, the methods, devices and systems encompassed by the disclosure herein are not limited to the description of FIGS. 2-6. As such, the methods, devices and systems described herein may be configured to measure variable parameters other than temperature, such as but not limited to pressure, acceleration, tension, force, volume, velocity, pH, oxygen concentration or humidity. Further, the methods described herein may be implemented in devices and systems other than for use with medical probes. For example, an electrocardiogram system could be configured to implement the methods described herein.

Turning back to FIG. 1, the method outlined therein includes, as denoted in blocks 12 and 14, measuring a voltage derived from the balanced circuit which correlates to a common mode signal of the balanced circuit and further determining, from the measured voltage, a value of the parameter. Applications of such steps in the method outlined in FIG. 2 are respectively denoted in blocks 22 and 24. In particular, the method outlined in FIG. 2 includes block 20 for positioning a resistive sensor (e.g., a piezoresistive sensor) such that at least two variable resistors of a Wheatstone bridge circuit of the sensor are arranged in an environment in which temperature is to be measured. Thereafter, block 22 includes measuring a temperature detection voltage while the two variable resistors are arranged in the environment and, then at block 24, a temperature of the environment is determined from the measured temperature detection voltage. It is noted that when a Wheatstone bridge circuit includes more than two variable resistors, two or more (and possibly all) of the variable resistors may be arranged in the environment in which temperature is to be measured and, thus, the process of measuring the temperature detection voltage may be when two or more (and possibly all) of the variable resistors are arranged in the environment.

As denoted in block 22, the temperature detection voltage is measured between a first voltage derived from the Wheatstone bridge circuit which is proportional to a summed voltage of signal output nodes of the Wheatstone bridge circuit and a second voltage which is proportional to a reference voltage for the Wheatstone bridge circuit. The operation of such steps may be better understood when described in relation to the exemplary circuits depicted in FIGS. 3-5 as set forth below. In general, however, the processes outlined in blocks 12, 14, 22 and 24 of FIGS. 1 and 2 are directed to measuring a common mode signal of a balanced circuit and using the common mode signal to determine a value of a parameter of an object or an environment. This is contrast to conventional techniques of monitoring common mode signals against predetermined thresholds to simply accept or reject a differential mode signal measurement.

In addition to steps 12 and 14, the method of FIG. 1 may, in some embodiments, include measuring a differential mode voltage of the balanced circuit as denoted in block 16 and further determining from the differential mode voltage a value of another distinct parameter of the object or environment in which at least part of the balanced circuit is arranged as denoted in block 18. Applications of such steps in the embodiment of FIG. 2 are outlined in blocks 26 and 28, specifically measuring a differential voltage between signal output nodes of the Wheatstone bridge circuit and determining from the differential voltage measurement a pressure of the environment. As with the description of the processes outlined in blocks 12, 14, 22 and 24, the operation of the processes outlined in blocks 16, 18, 26 and 28 may be better understood when described in relation to the exemplary circuits depicted in FIGS. 3-5 as set forth below. As noted above, the processes outlined in blocks 12, 14, 22 and 24 of FIGS. 1 and 2 are directed to using a common mode signal to determine a value of a parameter of an object or an environment. Combining such a technique with measuring a differential mode signal to determine a value of another parameter of an object or environment as outlined in blocks 16, 18, 26 and 28 advantageously increases the functionality of balanced circuit sensors for determining more information of interest. In some cases, combining the techniques may allow fewer sensors to be used for an evaluation of an object or an environment. For example, the method discussed in reference to FIG. 2 may obviate a need for a temperature sensor distinct from the resistive sensor in a system.

The dotted lines between some of the blocks in FIG. 1 denote that the operations outlined in blocks 16 and 18 may be conducted prior to, subsequent to, or at substantially the same time as the operations outlined in blocks 12 and 14. Likewise, the dotted lines between the some of the blocks in FIG. 2 denote that the operations outlined in blocks 26 and 28 may be conducted prior to, subsequent to, or at substantially the same time as the operations outlined in blocks 22 and 24. In some cases, it may be advantageous (i.e., time effective) for the processes outlined in blocks 14 and 18 to be performed simultaneously. Likewise, it may be desirable (i.e., time effective) for the processes outlined in blocks 24 and 28 to be performed simultaneously in some embodiments. In any case, the dotted lines around blocks 16, 18, 26 and 28 in FIGS. 1 and 2 denote the processes outlined therein are optional. In particular, it is noted that the methods, devices and systems described herein may be performed to determine a value of a single parameter of an object or environment and do not need to include measuring a differential mode voltage of the balanced circuit or determining a parameter value therefrom. To this end, it is noted that although a resistive sensor (e.g., a piezoresistive sensor) may include elements which are operationally sensitive to changes in environmental pressure as described above, the sensor need not be used to measure pressure in an environment. The resistive sensor could be simply used to measure temperature of that environment. Alternatively, the resistive sensor could be used to measure both pressure and temperature of the environment as described above.

As noted above, the circuits depicted in FIGS. 3-5 are examples of which may be employed for the method outlined in FIG. 2. Other circuits employing additional, fewer and/or different elements, however, may be employed to effect the operations outlined in FIG. 2. For example, although a Wheatstone bridge having two variable resistors and two fixed resistors (commonly referred to as a halfbridge circuit) is specifically described in reference to FIGS. 3-5, silicon strain gauges having four variable resistors (commonly referred to as full-bridge circuits) may be alternatively used. Furthermore, different summation circuitry may be employed for the temperature detection circuitry described in reference to FIGS. 3-5. Moreover, different reference voltage circuitry other than what is disclosed in reference to FIGS. 4-5 may be used. In some cases, the summation operations described in reference to FIGS. 3-5 may be partially or wholly done via software (i.e., via processor-executable program instructions) instead of partially or wholly via circuitry. In other words, the temperature detection circuitry described in reference to FIGS. 3-5 may, in some cases, be partially or wholly substituted by software having program instructions for performing such computational operations. A particularly suitable application of such is to have computational program instructions disposed on or accessible by an electronic monitoring system which is in electrical communication with the device comprising the balanced circuit as described in more detail below in reference to FIG. 6.

Turning to FIG. 3, circuit 30 is shown having Wheatstone bridge 32 coupled between power supply 34 and reference 36. Reference 36 may be ground or any node of circuit 30 common to Wheatstone bridge 32. The specifications of power supply 34 may generally depend on the application in which the circuit is employed and, thus, may vary widely among systems. An exemplary specification for power supply 34 when circuit 30 is applied within a medical probe system, for example, may be a maximum of 5 volts, but specifications of larger and smaller voltages may be employed. In some cases, circuit 30 may include potentiometer 38 for adjusting the level of the power transmitted to Wheatstone bridge 32 as shown in FIG. 3, but such an element is optional. It is noted that the dotted line to which numeral 32 refers to in FIG. 3 is used to schematically indicate which elements of circuit 30 makeup Wheatstone bridge 32. The dotted line to which numeral 32 refers is not part of the circuit nor does it indicate that Wheatstone bridge 32 is an optional element in circuit 30.

As shown in FIG. 3, Wheatstone bridge 32 may include two variable resistors 40 and 42 and two fixed resistors 44. In some embodiments, variable resistors 40 and 42 may be configured to be operationally sensitive to changes in pressure in an environment in which they are arranged. In particular, one of variable resistors 40 and 42 may be configured to increase in resistance with a change in environmental pressure and the other variable resistor may be configured to decrease in resistance with the change in environmental pressure. An example of a Wheatstone bridge having such characteristics is one which has variable resistors 40 and 42 made of a semiconductive material and, thus, the Wheatstone bridge serves as a piezoresistive sensor. In any case, ensuing to a design of varying resistance with changes in environmental pressure, a differential mode voltage of Wheatstone bridge 32 (i.e., a differential voltage between signal output nodes 46 and 48) may be measured and then used to determine (i.e., quantitate) the pressure of the environment in which the variable resistors are arranged as noted in FIG. 3. Such process steps are denoted in blocks 26 and 28 of FIG. 2. In alternative embodiments, variable resistors 40 and 42 may be configured to be operationally sensitive to changes in a parameter other than pressure, such as but not limited to temperature, humidity, force, tension, volume, velocity, pH, oxygen concentration and acceleration. In such cases, the differential mode measurement will accordingly be used to quantitate the noted parameter.

As further shown in FIG. 3, circuit 30 may optionally include compensation circuitry 49 coupled to Wheatstone bridge 32. In general, compensation circuitry 49 is configured to compensate for variations of a resistive coefficient of a conductive material comprising the Wheatstone bridge circuit, specifically variable resistors 40 and 42, due to ambient temperature changes of the conductive material. For example, in embodiments in which variable resistors 40 and 42 are made of a semiconductive material, compensation circuitry 49 may be configured to compensate for variations of a piezoresistive coefficient of the semiconductive material due to ambient temperature changes of the semiconductive material. There are a wide variety of manners known in the art in which to compensate for temperature changes and, thus, compensation circuitry 49 is depicted very generally in FIG. 3 so as to not limit the scope to which it may be. An example of compensation circuitry which may be used is one or more fixed resistors in parallel with at least one of variable resistors 40 and 42 of Wheatstone bridge 32. It is noted that the compensation circuitry is not limited to when Wheatstone bridge 32 includes two variable resistors and, more specifically, may be employed when Wheatstone bridge 32 includes any plurality of variable resistors.

In any case, with the inclusion compensation circuitry 49 in circuit 30, the accuracy of the differential mode measurement of Wheatstone bridge 32 in relation to a parameter of interest may be improved. In particular, compensation circuitry 49 may aid in counteracting changes in pressure sensitivity of a conductive material comprising Wheatstone bridge 32 due to temperature changes such that resistance changes of variable resistors 40 and 42 are maintained substantially uniform with pressure changes regardless of the ambient temperature. Although compensation circuitry may be beneficial in some cases, it is not required for the methods, devices and systems described herein. In particular, a balanced circuit may be void of such compensation circuitry if the effects on pressure sensitivity are not large enough to warrant significant inaccuracy of a differential mode measurement from the circuit.

In any case, circuit 30 may include temperature detection circuitry 50 coupled to Wheatstone bridge 32 as shown in FIG. 3. Similar to the dotted line encompassing the elements of Wheatstone bridge 32, the dotted line to which numeral 50 refers to in FIG. 3 is used to schematically indicate which elements of circuit 30 makeup temperature detection circuitry 50. The dotted line to which numeral 50 refers is not part of the circuit nor does it indicate that temperature detection circuitry 50 is an optional element in circuit 30. FIG. 3 depicts temperature detection circuitry 50 including two signal lines coupled to Wheatstone bridge 32. As one skilled in the art would be aware, the signal lines are effectively coupled to signal output nodes 46 and 48 of Wheatstone bridge 32. Direct coupling to the signal output nodes is not shown in FIG. 3 to simplify the depiction of temperature detection circuitry 50.

As shown in FIG. 3, the signal lines of temperature detection circuitry 50 include fixed resistors 52 and 54, respectively, and are joined to form a closed loop. Such a design, in effect, produces a measurable voltage at node 56 which is proportional to a summed voltage of signal output nodes 46 and 48 of Wheatstone bridge 32. Alternatively stated, a measurable voltage is generated at node 56 which is proportional to a summation of the voltages at the output nodes of Wheatstone bridge 32. In yet other words, the design produces a measurable voltage at node 56 which correlates to a common mode signal of Wheatstone bridge 32. As used herein, the term "common mode signal" refers to the average value of signals at the positive and negative output nodes of a differential circuit. A quantitative measure of a common mode signal is referred to as common mode voltage, which as noted above refers to the voltage at a given location that appears equally and in phase from each signal conductor to a common reference. Alternatively stated, the term "common mode voltage" refers to the instantaneous algebraic average of two signals within a balanced circuit with both signals referenced to a common reference.

Depending on the resistances of resistors 52 and 54, the voltage measured between nodes 56 and 58 may be the common mode voltage of Wheatstone bridge 32 or may be of greater or lesser proportion thereto. In particular, when the resistances of resistors 52 and 54 are substantially equal, the voltage measured between nodes 56 and 58 is the common mode voltage of Wheatstone bridge 32. In some cases, however, it may be advantageous to produce a voltage which is larger or smaller than the common mode voltage of Wheatstone bridge 32 and, thus, in some cases, resistors 52 and 54 may have different resistances. For example, it may be desirable to produce a voltage which is larger than the common mode voltage of Wheatstone bridge 32 such that a voltage reading between nodes 56 and 58 may be amplified. In particular, an amplified voltage measurement between nodes 56 and 58 may aid in ascertaining a temperature of the object or environment in which at least variable resistors 40 and 42 of Wheatstone bridge 32 are disposed. Regardless of whether the voltage measured between nodes 56 and 58 is the common mode voltage of Wheatstone bridge 32 or is of greater or lesser proportion thereto, the measured voltage may be referenced as correlating to a common mode signal of Wheatstone bridge 32 since the measured voltage is in relationship with the average value of signals at the signal output nodes of Wheatstone bridge. As used herein, the term "proportional" means corresponding in value by a set ratio, wherein the ratio is a non-negative number (whole or fractional) that is less than, equal, or greater than 1. As such, the term "proportional" is inclusive to values which are the same as well as those which are non-negative multiples of each other.

As shown in FIG. 3, a voltage reading between nodes 56 and 58 may relate to temperature, particularly when Wheatstone bridge 32 includes resistive elements as described above. In view thereof, the voltage reading between nodes 56 and 58 is sometimes referred to herein as "a temperature detection voltage." In other embodiments, the voltage reading between nodes 56 and 58 may relate to a different variable parameter of an object or environment, depending on the sensitivity of resistors 40 and 42 to different parameters. In any case, the voltage reading between nodes 56 and 58 is used to determine a value of a parameter of interest for an object or environment. More specifically, a computational correlation between a parameter and voltage readings between nodes 56 and 58 of circuit 30 may be predetermined and the correlation may be used to determine the value of the parameter from a given voltage reading. In some cases, the computational correlation may be a polynomial equation having a voltage reading between nodes 56 and 58 of circuit 30 as a variable. Accordingly, the process outlined in block 24 of FIG. 2 may include computing temperature of the environment from a polynomial equation having the temperature detection voltage as a variable. In some cases, the polynomial equation may be a first degree polynomial equation (i.e., a linear equation), but polynomial equations of larger degrees are possible.

As noted above, the circuits depicted in FIGS. 4 and 5 offer additional examples which may be employed for the method outlined in FIG. 2. The circuits of FIGS. 4 and 5 are similar to circuit 30 depicted in FIG. 3 in that they include Wheatstone bridge 32 and optional potentiometer 38 coupled between power supply 34 and reference 36 and further include optional compensation circuitry 49. The specifics of such elements discussed above with respect to FIG. 3 may be applied to the circuits depicted in FIGS. 4 and 5 and are not reiterated for the sake of brevity. As set forth in more detail below, the circuits of FIGS. 4 and 5 differ from circuit 30 depicted in FIG. 3 by the inclusion of different temperature detection circuitry as well as reference voltage circuitry configured to generate a biased reference voltage relative to an excitation voltage applied to Wheatstone bridge 32. The disclosure of the different temperature detection circuitry in FIGS. 4 and 5 emphasizes that the voltage derived from Wheatstone bridge 32 may be of any proportion to a summed voltage of signal output nodes of the Wheatstone bridge. Furthermore, as set forth in more detail below, the inclusion of reference voltage circuitry in the circuits of FIGS. 4 and 5 discloses that the "second voltage" specified in block 22 of FIG. 2 may, in some embodiments, be in reference to power supply 34 rather than just in reference to reference 36 as depicted in FIG. 3. As such, it is noted that the phrase "reference voltage for the Wheatstone bridge" denoted in block 22 of FIG. 2 can refer to either the excitation source or a common reference of a Wheatstone bridge.

As shown in FIG. 4, circuit 60 includes temperature detection circuitry 62 as well as resistors 70 and 72 between power supply 34 and reference 36. In general, resistors 70 and 72 makeup exemplary reference voltage circuitry which is configured to generate a biased reference voltage at node 74 relative to an excitation voltage applied to Wheatstone bridge 32. In other words, resistors 70 and 72 bias reference 36 to power supply 34 such that the voltage to which the output voltage from temperature detection circuitry 62 is referenced may be set to a predetermined value relative to power supply 34. An example of a bias is half of power supply 34, but resistors 70 and 72 may be configured to generate other proportions of power supply 34. It is noted that resistors 70 and 72 are merely an example of reference voltage circuitry which may be used to bias reference 36 to power supply 34. Any biasing techniques known to those skilled in art may be used in circuit 60 and, thus, the methods, devices and system described herein are not necessarily limited to the embodiment depicted in FIG. 4.

Temperature detection circuitry 62 of FIG. 4 differs from temperature detection circuitry 50 of FIG. 3 by the inclusion of buffers 64 and 66 as well as potentiometer 68 instead of resistors 52 and 54. Buffers 64 and 66 may be generally configured to ensure that the voltage reading between potentiometer 68 and node 74 does not have a loading effect on the differential mode measurement between signal output nodes 46 and 48 of Wheatstone bridge 32. Potentiometer 68 may be configured to match an incoming signal at a particular reference temperature to that of the biased signal at node 74 such that voltage output for that temperature would be zero volts. Such a design may aid in simplifying the determination of temperature from a given temperature detection voltage. As with the reference voltage circuitry of resistors 70 and 72, the use of buffers 64 and 66 is merely an example of circuitry which may be used to ensure that a loading effect is not imposed on Wheatstone bridge 32. Likewise, the use of potentiometer 68 with biasing circuitry is merely an example in which to null out a voltage reading for a particular temperature. Other techniques known to those skilled in art may be used in circuit 60 and, thus, the methods, devices and system described herein are not necessarily limited to the embodiment depicted in FIG. 4.

As shown in FIG. 5, circuit 80 differs from circuit 60 depicted in FIG. 4 by inclusion of temperature detection circuitry 82 as well as buffer 76 from node 74. Circuit 80 includes resistors 70 and 72 as is included in circuit 60 of FIG. 4. In addition, temperature detection circuitry 82 includes buffers 64 and 66 as well as potentiometer 68 as is included in temperature detection circuitry 62 of FIG. 4. The specifics of such elements discussed above with respect to FIG. 4 may be applied to circuit 80 depicted in FIG. 5 and are not reiterated for the sake of brevity. As shown in FIG. 5, temperature detection circuitry 82 includes amplifier 84 and amplifier calibrator controls 86. In general, amplifier 84 adjusts voltage output from potentiometer 68 based on the presets in amplifier calibrator controls 86. Such circuitry allows for bi-directional voltage output depending on the null output voltage adjustment of potentiometer 68. Buffer 76 offers impedance isolation from power supply 34 and reference 36 to improve the temperature detection voltage reading from circuit 80 relative to circuits 30 and 60 of FIGS. 3 and 4. It is noted that use of buffer 76, amplifier 84, and amplifier calibrator controls 86 are merely examples of circuitry which may be used to offer impedance isolation and amplify signals. Other techniques known to those skilled in art may be used in circuit 80 and, thus, the methods, devices and system described herein are not necessarily limited to the embodiment depicted in FIG. 5.

As set forth above, the methods, systems and devices considered herein may be used to determine any measurable parameter of interest which relates to the operationally sensitive elements of a balanced circuit and, moreover, may be used on or within any object or environment in which a device having the balanced circuit can access. As merely an example of a system which may be configured to perform the methods described herein, FIG. 6 depicts a schematic diagram of medical probe system 90 having a device which includes circuitry by which to measure a voltage derived from a balanced circuit arranged within medical probe 92 which correlates to a common mode signal of the balanced circuit. In addition, medical probe system 90 includes processor executable program instructions 102 for determining from the measured voltage a temperature of an environment in which a tip of medical probe 92 is arranged. As described in more detail below, an alternative configuration to medical probe system 90 is to incorporate the computational operations of temperature detection circuitry 96 and/or the reference voltage circuitry described below into program instructions 102, thus negating the inclusion of either or both of such circuitry within the system.

In any case, the medical probe systems described in reference to FIG. 6 (including variations to the depiction in FIG. 6) may be used for any application using a medical probe in which temperature of bodily fluids, cavities or tissue may be of interest and/or temperature of fluids administered into a body via a catheter may be of interest. Examples of applications include but are not limited to the drainage or administration of fluids into a body, measuring/monitoring arterial or vein blood pressure, measuring/monitoring pressure of body cavities, and thermodilution techniques. It is noted that medical probe system 90 is merely an example of a system which may be configured to perform the methods described herein. Other medical probe systems including devices and features additional or alternative to those described in reference to FIG. 6 may be suitable as well. In addition, a variety of other types of systems in any field may be configured to perform the methods described herein, particularly any of which involve differential signal processing.

In general, medical probe 92 of medical probe system 90 may include any type of medical probe, i.e., medical probe 92 may be a medical probe of any size, material, type, purpose, etc. and may be a single or multiple tipped medical probe. The term "medical probe," as used herein, refers to a long, slender instrument for exploring wounds, body cavities, or body passages. Thus, the term "medical probe" encompasses catheters as well as devices including no lumen. In general, the term "catheter" as used herein is inclusive to catheters having an open lumen (i.e., having an unblocked lumen) as well as catheters having a closed lumen (i.e., a lumen having an obstruction such that the catheter cannot be used for the passage of fluid). As common to all medical probes, medical probe 92 includes at least one tip 93 which is used to access a particular bodily fluid, body part or body region. Specific to the medical probes considered herein, tip 93 includes at least a portion of a balanced circuit, particularly elements of a balanced circuit which are operationally sensitive to a parameter of a bodily fluid, a body part or a body region. The balanced circuit may be of any type or configuration.

An example of a balanced circuit which may be suitable for a medical probe is a Wheatstone bridge with two variable resistors and two fixed resistors. Alternatively, a Wheatstone bridge having four variable resistors may be used. In yet other embodiments, another type of balanced circuit may be employed. In any case, the entire balanced circuit may be disposed within tip 93 in some embodiments. In other cases, however, less than the entire balanced circuit may be disposed within tip 93 and, in some embodiments, only the operationally sensitive elements of the balanced circuit may be disposed within tip 93. In particular, in some case, it may be desirable to minimize the size of tip 93 as well as the areal space of the medical probe tubing and, thus, it may be beneficial to include only a portion of a balanced circuit therein. In any of such cases, the remaining portion of the balanced circuit may be disposed in electrical connector 94 of medical probe 92 and/or or within the tubing of the medical probe.

As shown by operational connection 97 in FIG. 6, electrical connector 94 and electronic signal monitoring device 95 may be jointly configured for electrical communication with each other. In particular, electronic signal monitoring device 95 is configured to measure electrical parameters of the balanced circuit disposed within medical probe 92 and, thus, electrical connector 94 includes a means for sending output signals of the balanced circuit therein and electronic signal monitoring device 95 includes a means for receiving such output signals. In some embodiments, each of electrical connector 94 and electronic signal monitoring device 95 may include an electrical port configured for securely and operatively coupling with an electrical connector of the other (i.e., hard-wired input/output terminals). In such cases, the coupling may be direct or may be through intermediary means. In yet other embodiments, electrical connector 94 and electronic signal monitoring device 95 may additionally or alternatively include transmitters to transmit signals wirelessly. In any case, electronic signal monitoring device 95 may be configured to process data received from the balanced circuit disposed within medical probe 92, as described in more detail below with respect to means 98 and 99. In some embodiments, electronic signal monitoring device 95 may, be configured to supply power and ground to the balanced circuit within medical probe 92 as well as any other circuitry disposed therein. As such, electronic signal monitoring device 95 may, in some cases, include an excitation voltage terminal for supplying an excitation voltage to the balanced circuit disposed within medical probe 92 and also a reference common voltage terminal for supplying a reference common voltage for the balanced circuit.

As described above in reference to FIGS. 2-5, the methods, devices and systems described herein may utilize a resistive sensor (i.e., a balanced circuit having resistive elements) and, thus, in some embodiments, medical probe 92 may include a resistive sensor. In such cases, medical probe 92 may optionally include compensation circuitry coupled to the balanced circuit disposed therein. In general, as described above in reference to FIG. 3, the compensation circuitry is configured to compensate for variations of a resistive coefficient of a conductive material comprising the balanced circuit due to ambient temperature changes of the conductive material. As further described above, although compensation circuitry may be beneficial in some cases, it is not required for the methods, devices and systems described herein and, thus, medical probe 92 may be void of compensation circuitry in some embodiments. In any case, medical probe 92 may, in some cases, include reference voltage circuitry for generating a biased reference voltage relative to an excitation voltage applied to the balanced circuit disposed therein. In addition or alternatively, electronic signal monitoring device 95 and/or a device between medical probe 92 and electronic signal monitoring device 95 may include such circuitry. Examples of such circuitry are described in reference to FIGS. 4 and 5, but the scope of such is not so limited. In yet other embodiments, the computational operations of such reference voltage circuitry may be incorporated into program instructions 102, thus negating the inclusion of such circuitry within medical probe 92 and/or electronic signal monitoring device 95. In yet other embodiments, medical probe system 90 may be void of means to change values of a reference voltage.

In any case, medical probe system 90 may, in some embodiments, include temperature detection circuitry 96 as illustrated in FIG. 6. In general, temperature detection circuitry 96 is configured to generate a voltage which is proportional to a summed voltage of signal output nodes of the balanced circuit disposed within medical probe 92 (i.e., a voltage which is proportional to a summation of the voltages at the signal output nodes of the balanced circuit). Examples of circuitry are described in reference to FIGS. 3-5, but temperature detection circuitry 96 is not necessarily so limited. As denoted by the dotted lines extending from temperature detection circuitry 96 in FIG. 6, temperature detection circuitry 96 may be disposed within medical probe 92, electronic signal monitoring device 95, and/or between medical probe 92 and electronic signal monitoring device 95 (i.e., within an intermediary means between the devices). In cases in which temperature detection circuitry 96 is disposed within medical probe 92, temperature detection circuitry 96 may be disposed within tip 93 and/or electrical connector 94. As described above, an alternative configuration to medical probe system 90 is to incorporate the computational operations of temperature detection circuitry 96 into program instructions 102, thus negating the inclusion of such circuitry within the system.

As shown in FIG. 6, electronic signal monitoring device 95 may, in some cases, include means 98 for determining a voltage between the voltage generated by temperature detection circuitry 96 (or comparable program instructions) and another voltage which is proportional to the common reference voltage or the excitation voltage supplied to the medical probe. The voltage determined by means 98 is referred to herein as a temperature detection voltage since it is used to determine the temperature of the environment in which tip 93 is arranged, particularly by program instructions 102 in medical probe system 90. In particular, FIG. 6 shows medical probe system 90 with storage medium 100 including program instructions 102 coupled to electronic signal monitoring device 95 via input therefrom. In general, program instructions 102 are executable by processor 104 for generating output 106 and, more specifically, for determining, from the temperature detection voltage measured by means 98, a temperature of an environment in which tip 93 of medical probe 92 is arranged. Such a process may include any of the particularities described in reference to block 24 of FIG. 2 and are not reiterated for the sake of brevity. In some embodiments, electronic signal monitoring device 95 and storage medium 100 may be one of the same and, thus, in some cases, electronic signal monitoring device 95 may include program instructions 102. In other cases, storage medium 100 may be a device distinct from electronic signal monitoring device 95.

In general, the term "storage medium," as used herein, may refer to any electronic medium configured to hold one or more set of program instructions, such as but not limited to a read-only memory, a random access memory, a magnetic or optical disk, or magnetic tape. The term "program instructions" may generally refer to commands within a program which are configured to perform a particular function, such as receiving input, recording receipts of signals, and processing signals. Program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired. Program instructions implementing the processes described herein may be transmitted over on a carrier medium such as a wire, cable, or wireless transmission link.

As shown in FIG. 6, electronic signal monitoring device 95 may, in some embodiments, include means 99 for measuring a differential mode voltage of the balanced circuit disposed within medical probe 92, particularly via signals transmitted from electrical connector 94 of medical probe 92. In such cases, program instructions 102 may be further executable by processor 104 for determining, from the differential voltage, a pressure of the environment in which tip 93 is arranged. As such, medical probe system 90 may be used in such embodiments to determine temperature and/or pressure of the environment in which tip 93 is arranged. As described in detail above, a benefit of the methods, devices and systems described herein is that a balanced circuit may be used to monitor two variable parameters of an object or an environment. Hence, fewer sensors may be used for an evaluation of an object or an environment. As such, medical probe 92 may, in some embodiments, be absent a temperature sensor distinct from the temperature detection means dually provided by the balanced circuit disposed therein and temperature detection circuitry 96. Alternatively stated for cases in which medical probe 92 includes a resistive Wheatstone bridge and compensation circuitry, medical probe 92 may be absent a temperature sensor distinct from the resistive sensor made up by the Wheatstone bridge, the compensation circuitry and temperature detection circuitry 96. Such scenarios may be particularly advantageous when available space at tip 93 is limited. In any case, electronic signal monitoring device 95 may be configured to utilize means 98 and 99 at the same time or in succession.

It will be appreciated to those skilled in the art having the benefit of this disclosure that this invention is believed to provide methods, devices and systems which utilize a voltage reading associated with a common mode signal of a balanced circuit to determine a value of a parameter of an object or an environment. Further modifications and alternative embodiments of various aspects of the invention will be apparent to those skilled in the art in view of this description. For example, although the description of methods, devices and systems provided herein are specific to Wheatstone bridge circuits including resistive elements for determining temperature of an environment, the methods, devices and systems provided herein may be constructed with a variety of balanced circuits having any type of operationally sensitive elements for determining any type of variable parameter of an object or environment. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for determining temperature using a resistive sensor having a Wheatstone bridge circuit with at least two variable resistors, wherein the method comprises:
   positioning the resistive sensor such that the at least two variable resistors of the Wheatstone bridge circuit are arranged in an environment in which temperature is to be determined;
   measuring, while the two variable resistors are arranged in the environment, a temperature detection voltage derived from the Wheatstone bridge circuit which correlates to a common mode signal of the Wheatstone bridge circuit;
   determining, from the temperature detection voltage, a temperature of the environment;
   measuring a differential voltage between signal output nodes of the Wheatstone bridge circuit; and
   determining, from the differential voltage, a pressure of the environment, wherein at least one of the steps of measuring the differential voltage and determining the pressure is performed simultaneously with at least one of the steps of measuring the temperature detection voltage and determining the temperature.

2. The method of claim 1, wherein the method of determining the temperature comprises computing the temperature from a polynomial equation having the temperature detection voltage as a variable.

3. The method of claim 1, wherein the Wheatstone bridge circuit is a half-bridge circuit.

4. The method of claim 1, wherein the at least two variable resistors respectively comprise opposing sides of the Wheatstone bridge circuit during the steps of measuring the differential voltage and measuring the temperature detection voltage.

5. The method of claim 1, wherein the resistive sensor is disposed within a medical probe.

6. An electronic signal monitoring device for monitoring and processing signals received from a balanced circuit of a medical probe, wherein the electronic signal monitoring device comprises:
   a first means for receiving output signals from the balanced circuit;
   a second means for determining from one or more of the received output signals a voltage which correlates to a common mode signal of the balanced circuit;
   a third means for measuring a differential mode voltage of the balanced circuit, wherein the electronic signal monitoring device is configured to utilize the third means and the second means to measure the differential voltage and the voltage correlating to a common mode signal of the balanced circuit substantially simultaneously; and
   program instructions which are executable by a processor for:
      determining, from the voltage which correlates to a common mode signal of the balanced circuit, a temperature of an environment in which a tip of the medical probe is arranged; and
      determining, from the differential voltage, a pressure of the environment.

* * * * *